United States Patent
Nishida et al.

(10) Patent No.: US 11,452,683 B2
(45) Date of Patent: Sep. 27, 2022

(54) COSMETIC PRODUCT

(71) Applicant: SHISEIDO COMPANY, LTD., Tokyo (JP)

(72) Inventors: Keita Nishida, Kanagawa (JP); Takumi Watanabe, Kanagawa (JP); Megumi Kinoshita, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/494,591

(22) PCT Filed: Mar. 26, 2018

(86) PCT No.: PCT/JP2018/012033
§ 371 (c)(1),
(2) Date: Sep. 16, 2019

(87) PCT Pub. No.: WO2018/181126
PCT Pub. Date: Oct. 4, 2018

(65) Prior Publication Data
US 2020/0085721 A1 Mar. 19, 2020

(30) Foreign Application Priority Data

Mar. 31, 2017 (JP) .............................. JP2017-073076

(51) Int. Cl.
*A61K 8/891* (2006.01)
*A45D 33/02* (2006.01)
(Continued)

(52) U.S. Cl.
CPC .............. *A61K 8/891* (2013.01); *A45D 33/02* (2013.01); *A45D 33/34* (2013.01); *A61K 8/25* (2013.01);
(Continued)

(58) Field of Classification Search
CPC . A61K 8/891; A61K 8/25; A61K 8/26; A61K 8/29; A61K 2800/413;
(Continued)

(56) References Cited

U.S. PATENT DOCUMENTS

| | | | |
|---|---|---|---|
| 2003/0202993 A1 | 10/2003 | Sato | |
| 2010/0129301 A1* | 5/2010 | Tanaka | A61Q 19/00 424/59 |
| 2015/0320673 A1* | 11/2015 | Shimizu | A61K 8/891 424/64 |

FOREIGN PATENT DOCUMENTS

| | | | |
|---|---|---|---|
| CN | 101208073 | 6/2008 | |
| DE | 000020018677 | * 4/2002 | A61Q 5/06 |

(Continued)

OTHER PUBLICATIONS

Making Cosmetics Inc., Titanium Dioxide, accessed 2020, pp. 1-4. (Year: 2020).*

(Continued)

*Primary Examiner* — Trevor Love
(74) *Attorney, Agent, or Firm* — Rankin, Hill & Clark LLP

(57) ABSTRACT

A thickened composition for a cosmetic product including a content that is taken through a mesh contains a fine particulate powder and a silicone crosspolymer having a structure where dimethicone is cross-linked with an organic group, and has a storage modulus G'≥3000 Pa, as measured with a rheometer under the conditions of a gap of 0.5 mm, a strain oscillation angle of 0.1%, a frequency of 1 Hz, and a temperature of 25° C. while increasing stress applied with a 25 mm φ cone plate, and a loss tangent tan δ≤0.2, as calculated as a loss modulus G" measured under the same conditions divided by the storage modulus G'. A cosmetic product includes a container including an inner lid with a tight mesh and an outer lid for tightly closing a container (Continued)

body, and the thickened composition contained in the container body under the inner lid.

14 Claims, 1 Drawing Sheet

(51) Int. Cl.

| | | |
|---|---|---|
| *A45D 33/34* | (2006.01) | |
| *A61K 8/25* | (2006.01) | |
| *A61K 8/26* | (2006.01) | |
| *A61K 8/29* | (2006.01) | |
| *A61Q 1/00* | (2006.01) | |
| *A61Q 1/02* | (2006.01) | |
| *A45D 33/00* | (2006.01) | |
| *A45D 33/06* | (2006.01) | |
| *A61Q 1/12* | (2006.01) | |
| *A61Q 1/10* | (2006.01) | |

(52) U.S. Cl.
CPC .................. *A61K 8/26* (2013.01); *A61K 8/29* (2013.01); *A61Q 1/00* (2013.01); *A61K 2800/413* (2013.01); *A61K 2800/48* (2013.01)

(58) Field of Classification Search
CPC .... A61K 2800/48; A45D 33/02; A45D 33/34; A45D 33/0033; A45D 33/06; A61Q 1/00; A61Q 1/02; A61Q 1/12
See application file for complete search history.

(56) References Cited

FOREIGN PATENT DOCUMENTS

| EP | 2556822 A1 | 2/2013 |
|---|---|---|
| JP | 743575 U | 9/1995 |
| JP | 2001002522 A | 1/2001 |
| JP | 2002284629 A | 10/2002 |
| JP | 3812733 B2 | 8/2006 |
| JP | 2008194190 A | 8/2008 |
| JP | 2012047667 A | 3/2012 |
| JP | 2012-184206 A | 9/2012 |
| JP | 2015020974 A | 2/2015 |
| JP | 2016124860 A | 7/2016 |
| JP | 2016220871 A | 12/2016 |
| WO | 2016030841 A2 | 3/2016 |

OTHER PUBLICATIONS

DE000020018677 Machine Translation, 2002, pp. 1-4. (Year: 2002).*
International Search Report dated Aug. 7, 2018 filed in PCT/JP2018/012033; Partial translation.
Written Opinion of the International Searching Authority dated Aug. 7, 2018 filed in PCT/JP2018/012033; Partial translation.
Extended European Search Report (EESR) dated Oct. 22, 2020 issued in corresponding European Patent Application No. 18778254.5.
European Office Action dated Jul. 1, 2021 issued in corresponding European Patent Application No. 18778254.5.
European Office Communication dated Sep. 15, 2021 for corresponding European Patent Application No. 18778254.5, 4 pages.
Chinese Office Action (CNOA) dated Jan. 25, 2022 issued for the corresponding Chinese patent application No. 201710356768.6 and its English translation.
Japanese Office Action dated Apr. 27, 2022 for corresponding Japanese Patent Application No. 2019-509769; English translation.
Chinese Office Action dated Jul. 15, 2022 for Chinese Patent Application No. 201710356768.6; English translation.

* cited by examiner

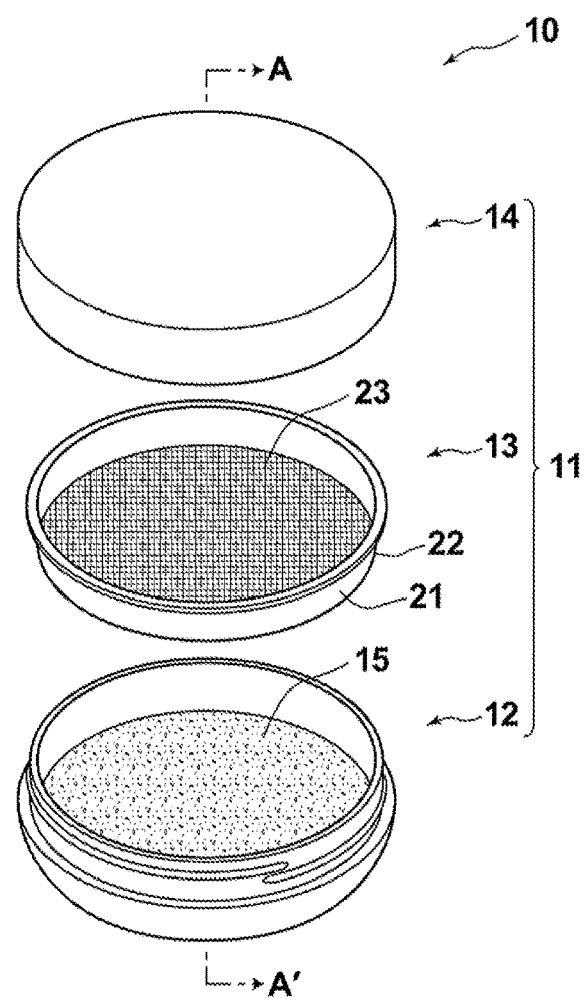
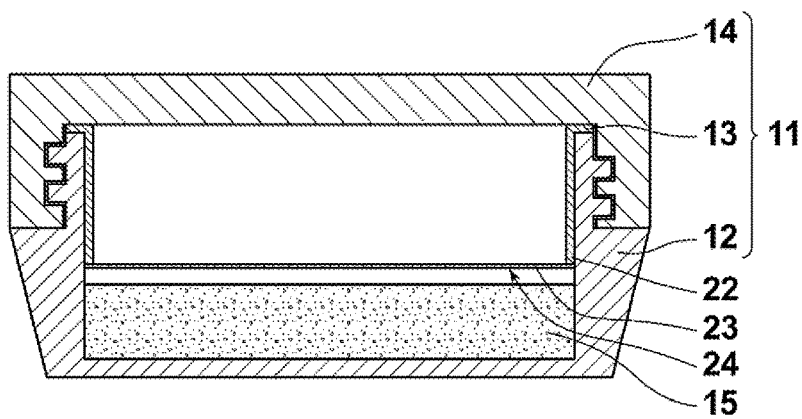
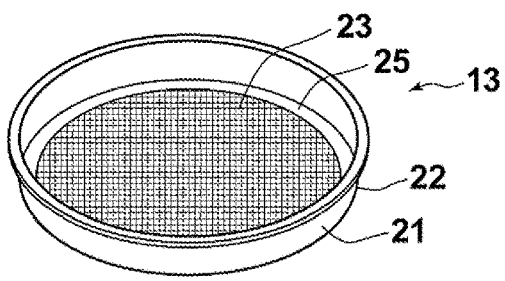

COSMETIC PRODUCT

TECHNICAL FIELD

The present disclosure relates to a thickened composition, and a cosmetic product including a container and the composition contained in the container.

BACKGROUND ART

In recent years, cosmetic containers with an inner lid provided with a tight stretchy mesh are known (see, for example, Patent Literature 1). Such cosmetic containers are configured such that, when the user presses the mesh with a hand, a cosmetic contained in the container body oozes out from the upper surface of the mesh. Then, the user takes the oozed-out cosmetic with a puff to apply the cosmetic to the skin of the face, or the like.

Further, Patent Literature 2 discloses a powder-in-oil (P/O) whipped oil-based composition containing bubbles. Such compositions take a form called whip-type, souffle-type, marshmallow-type, or paste-type. Regardless of high contents of oil-based components, such compositions can provide fluffy and elastic feeling and light feel during use, and has excellent powder dispersibility and long-term preservability.

CITATION LIST

Patent Literature

[PTL 1] Japanese Unexamined Patent Publication No. 2016-220871
[PTL 2] Japanese Unexamined Patent Publication No. 2015-20974

SUMMARY OF DISCLOSURE

Technical Problem

The bubble-containing powder-in-oil (P/O) whipped oil-based compositions as described above (which are hereinafter referred to as "whipped oil-based compositions") are contained in a jar container or a tube container to be provided to consumers.

However, if a whipped oil-based composition, which contains bubbles and thus is elastic, is put in a jar container, it may not be easy for the user to adjust the amount of the composition to be taken with a hand from the jar container. Further, if a whipped oil-based composition, which contains bubbles, is put in a tube container, there is a problem that the composition may be splashed when it is ejected from the tube.

In view of the above-described circumstances, the present disclosure is directed to providing a cosmetic product which allows an elastic composition, such as a whipped oil-based composition, to be taken well, to be uniformly spread when applied to the skin, and to provide smoothness and silky touch.

Solution to Problem

Namely, the cosmetic product of the present disclosure comprises:
a container comprising a container body having an upper opening, an inner lid provided with a tight mesh material, and an outer lid configured to tightly close the container body; and
a thickened composition contained in the container body under the inner lid such that the thickened composition is able to be taken through the mesh material,
wherein the thickened composition comprises:
a silicone crosspolymer having a structure where dimethicone is cross-linked with an organic group;
a fine particulate powder; and
a storage modulus G' of not less than 3000 Pa, which is measured with a rheometer under the conditions of a gap of 0.5 mm, a strain oscillation angle of 0.1%, a frequency of 1 Hz, and a temperature of 25° C. while increasing stress applied with a 25 mm φ cone plate, and a loss tangent tan δ of not more than 0.2, which is expressed by: loss modulus G"/storage modulus G'.

It is preferred that the silicone crosspolymer having a structure where dimethicone is cross-linked with an organic group be contained in an amount of not less than 2 mass % and not more than 10 mass % relative to the total mass of the thickened composition.

It is preferred that the silicone crosspolymer having a structure where dimethicone is cross-linked with an organic group be a dimethicone crosspolymer.

It is preferred that the mesh material have a mesh opening size of not less than 0.1 mm.

The mesh opening size, as used herein, is a value calculated according to the equation below:

$$A = (25.4/M) - d,$$

where A represents a mesh opening size (in mm), M represents mesh, and d represents a wire diameter (in mm).

The mesh M refers to the number of wires or the number of mesh openings within a length of 25.4 mm (1 inch).

It is preferred that the fine particulate powder be contained in an amount of not less than 1 mass % and not more than 15 mass % relative to the total mass of the thickened composition.

It is preferred that the fine particulate powder have an average primary particle diameter of not more than 1 μm.

It is preferred that the fine particulate powder be at least one selected from silica, bentonite, and titanium dioxide.

The thickened composition may contain water.

It is preferred that the thickened composition be taken using a puff.

Advantageous Effects of Disclosure

According to the cosmetic product of the present disclosure, the thickened composition is taken through the mesh material, and this allows the elastic thickened composition to be adequately taken, to be uniformly spread when applied to the skin, and to provide smoothness and silky touch.

BRIEF DESCRIPTION OF THE DRAWINGS

FIG. 1 is a schematic perspective view illustrating one embodiment of a cosmetic product of the present disclosure,
FIG. 2 is a cross-sectional view taken along line A-A' in FIG. 1, and
FIG. 3 is a schematic perspective view illustrating another example of an inner lid of the disclosure.

DESCRIPTION OF EMBODIMENTS

Hereinafter, details of a cosmetic product of the present disclosure will be described. FIG. 1 is a perspective view illustrating one embodiment of the cosmetic product of the disclosure.

As shown in FIG. 1, a cosmetic product 10 of the disclosure includes a container 11, which includes a container body 12 having an upper opening, an inner lid 13 provided with a tight mesh material 23, and an outer lid 14 configured to tightly close the container body 12, and a thickened composition 15 contained in the container body 12 under the inner lid 13 such that the thickened composition 15 is taken through the mesh material 23.

The thickened composition 15 contains a fine particulate powder and a silicone crosspolymer having a structure where dimethicone is cross-linked with an organic group, and the thickened composition 15 has a storage modulus G' of not less than 3000 Pa, which is measured with a rheometer under the conditions of a gap of 0.5 mm, a strain oscillation angle of 0.1%, a frequency of 1 Hz, and a temperature of 25° C. while increasing stress applied with a 25 mm φ cone plate, and a loss tangent tan δ of not more than 0.2, which is expressed by: loss modulus G''/storage modulus G'.

FIG. 2 is a cross-sectional view taken along line A-A' in FIG. 1.

As shown in FIG. 2, the thickened composition 15 is contained with being spaced apart from the mesh material 23 such that the thickened composition 15 does no contact a bottom surface 24 of the mesh material 23. When the mesh material 23 is pressed, the mesh material 23 contacts the thickened composition 15 and the thickened composition 15 oozes out through mesh openings of the mesh material 23.

The distance between the surface of the thickened composition 15 and the bottom surface 24 of the mesh material 23 can be determined as appropriate with consideration to elastic modulus of the thickened composition 15 and stretchability of the mesh material.

Container

Next, the container 11 of the cosmetic product of the disclosure is described.

The container 11 of the disclosure includes the container body 12 having the upper opening, the inner lid 13 provided with the tight mesh material 23, and the outer lid 14 configured to tightly close the container body 12.

As shown in FIG. 1, the mesh material 23 is fixed to a lower end 22 of a frame 21 of the inner lid 13 with a predetermined tension applied thereto. The mesh material 23 may be fixed to the frame 21 with an adhesive, or the mesh material may be fixed during injection molding of the frame 21 by stretching the mesh material across a metal mold for molding the frame 21 such that the injected resin enters a part of mesh openings of the mesh material 23.

The mesh material 23 may or may not be stretchable; however, it is preferred that the mesh material 23 be stretchable. A preferred example of the mesh material 23 is one made of woven fibers. Examples of the material of the fibers may include PET (polyethylene terephthalate) polyurethane, polyester, and nylon.

The mesh material 23 has a mesh opening size of preferably not less than 0.1 mm, and more preferably not less than 0.2 mm. Providing the mesh opening size of not less than 0.2 mm allows taking an appropriate amount of the thickened composition through the mesh openings when the mesh material 23 is pressed. Further, the mesh opening size is preferably not more than 5 mm, and more preferably not more than 3 mm. Providing the mesh opening size of not more than 5 mm allows preventing the thickened composition from leaking through the mesh openings.

Further, the mesh material 23 has a wire diameter of preferably not less than 0.2 mm and not more than 1 mm, and more preferably not less than 0.2 mm and not more than 0.5 mm. It should be noted that the wire diameter can be measured using an optical microscope, or the like.

In the above-described embodiment, the inner lid 13 may be provided with an edge 25 for disposing the mesh material 23 at the bottom of the inner circumference, as shown in FIG. 3. In a case where the mesh material is not stretchable, a resilient member, such as a sponge or a spring, may be placed under the edge 25, such that the resilient member shrinks downward when the mesh is pressed and allows the mesh material to reach the thickened composition and allow the user to take the thickened composition.

Thickened Composition

The thickened composition of the disclosure contains a fine particulate powder and a silicone crosspolymer having a structure where dimethicone is cross-linked with an organic group, and has a storage modulus G' of not less than 3000 Pa, which is measured with a rheometer under the conditions of a gap of 0.5 mm, a strain oscillation angle of 0.1%, a frequency of 1 Hz, and a temperature of 25° C. while increasing stress applied with a 25 mm φ cone plate, and a loss tangent tan δ of not more than 0.2, which is expressed by: loss modulus G''/storage modulus G'.

It is preferred that the storage modulus G' be not more than 8000. It is preferred that the storage modulus G' be not less than 3000 Pa and not more than 8000 Pa. Providing the storage modulus G' of not less than 3000 Pa allows achieving smoothness and good spreadability. Providing the storage modulus G' of not more than 8000 Pa allows the thickened composition to be taken well and to be uniformly applied to the skin.

In the disclosure, the loss tangent tan δ is not more than 0.2. The loss tangent tan δ is preferably not less than 0.01, and more preferably not less than 0.1 and not more than 0.2.

Providing the loss tangent tan δ of not more than 0.2 allows providing silky touch. The loss tangent tan δ of not less than 0.01 allows providing smoothness and good spreadability.

It should be noted that the loss tangent tan δ is expressed by: loss modulus G''/storage modulus G'. Similarly to the storage modulus G', the loss modulus G'' of the thickened composition is a value measured with a rheometer under the conditions of a gap of 0.5 mm, a strain oscillation angle of 0.1%, a frequency of 1 Hz, and a temperature of 25° C. while increasing stress applied with a 25 mm φ cone plate.

An example of the rheometer used to measure the storage modulus G', G'' and the loss tangent tan δ of the thickened composition is a rheometer MCR301 available from Anton Paar.

Silicone Crosspolymer Having a Structure where Dimethicone is Cross-Linked with an Organic Group The silicone crosspolymer having a structure where dimethicone is cross-linked with an organic group (which may hereinafter be referred to as "dimethicone partial crosspolymer") used in the thickened composition of the disclosure is not particularly limited as long as it has a cross-linked structure, and usually, a partially cross-linked dimethicone is desirable.

Examples of the organic group may include an alkylene group, a polyglyceryl-containing group, a polyether-containing group, and an organopolysiloxane-containing group. Specific examples of the silicone crosspolymer having a structure where dimethicone is cross-linked with an organic group may include dimethicone crosspolymer, (dimethicone/polyglycerin) crosspolymer, (dimethicone/PEG) crosspolymer, (dimethicone/vinyl dimethicone) crosspolymer, and (dimethicone/phenyl vinyl dimethicone) crosspolymer. Among them, dimethicone crosspolymer is particularly preferred.

The dimethicone partial silicone crosspolymer may be swollen with a liquid oil component before use. Alternatively, a swollen product of the dimethicone partial crosspolymer may be obtained as a commercially available product. Examples of the commercially available swollen product of the dimethicone crosspolymer may include DIMETHICONE CROSSPOLYMER BLEND 9040 (a mixture of dimethicone crosspolymer and decamethylcyclopentasiloxane containing 12% cross-linked product (actual content)), DIMETHICONE CROSSPOLYMER BLEND 9041 (a mixture of dimethicone crosspolymer and dimethicone 5 mPa·s containing 16% cross-linked product (actual content)), DIMETHICONE CROSSPOLYMER BLEND 9045 (a mixture of dimethicone crosspolymer and decamethylcyclopentasiloxane containing 12.5% cross-linked product (actual content)) (all of which are available from Dow Corning Toray Silicone), etc.

In the disclosure, the silicone crosspolymer having a structure where dimethicone is cross-linked with an organic group is contained preferably in an amount of not less than 2 mass % and not more than 10 mass %, and more preferably in an amount of not less than 3 mass % and not more than 8 mass % relative to the total mass of the thickened composition.

Including the silicone crosspolymer in an amount of not less than 2 mass % allows providing sufficient uniformity when the thickened composition is applied, and good usability. Further, including the silicone crosspolymer in an amount of not more than 10 mass % allows providing silky touch and smooth feel during use.

Fine Particulate Powder

In the disclosure, a fine particulate powder having an average primary particle diameter of not more than 1 μm, and preferably not more than 0.1 μm is used. The average primary particle diameter can be measured using a scanning electron microscope.

The fine particulate powder is not particularly limited as long as it has a particle diameter within this range; however, it is preferred that the fine particulate powder be at least one selected from silica, a fine particulate clay mineral, such as bentonite, and titanium dioxide.

The fine particulate powder is contained preferably in an amount of not less than 1 mass % and not more than 15 mass %, and more preferably in an amount of not less than 2 mass % and not more than 10 mass % relative to the total mass of the thickened composition. Including the fine particulate powder in an amount of not less than 1 mass % allows providing fluffy and elastic feel. Further, including the fine particulate powder in an amount of not more than 15 mass % allow providing light feel while maintaining the fluffy and elastic feel.

The fine particulate powder may have a particle, shape that is spherical, tabular, spindle-like, petal-like, or indefinite shape, and a spherical particle shape is more preferred, although the particle shape is not particularly limited. Preferred examples of the fine particulate powder may include inorganic powders, such as fine particulate silica, fine particulate titanium dioxide, fine particulate clay mineral, etc. The inorganic powder may be subjected to a surface treatment, such as hydrophobizing treatment or hydrophilizing treatment, as long as the effects of the disclosure are not impaired; however, it is preferred that the inorganic powder be not subjected to a surface treatment.

The thickened composition of the disclosure may also contain oil components, other powder components, or water, besides the fine particulate powder and the silicone crosspolymer having a structure where dimethicone is cross-linked with an organic group.

Oil Components

Preferred examples of the oil components may include: a hydrocarbon oil, such as liquid paraffin, ozokerite, squalene, pristane, paraffin, ceresin, squalane, or vaseline; a polar oil component, such as liquid lanolin, isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkylglycol monoisostearate, neopentylglycol dicaprate, diisostearyl malate, glycerin di-2-heptyl undecylenate, trimethylol propane tri-2-ethylhexylate, trimethylol propane triisostearate, pentaerythritol tetra-2-ethylhexylate, glycerin tri-2-ethylhexylate, trimethylol propane triisostearate, cetyl-2-ethylhexanoate, 2-ethylhexyl parmitate, glycerin trimyristate, glyceride tri-2-heptyl undecylenate, castor oil fatty acid methylester, oleic acid, acetoglyceride, 2-heptyl undecyl palmitate, diisopropyl adipate, N-lauroyl-L-glutamic acid-2-octyldodecyl ester, di-2-heptyl undecyl adipate, ethyl laurate, di-2-ethylhexyl sebacate, 2-hexyl decyl myristate, 2-hexyl decyl palmitate, 2-hexyl decyl adipate, diisopropyl sebacate, 2-ethylhexyl succinate, ethyl acetate, butyl acetate, amyl acetate, or triethyl citrate; a higher alcohol, such as stearyl alcohol, behenyl alcohol, oleyl alcohol, or cetostearyl alcohol; and a vegetable oil, such as jojoba oil, olive oil, nut oil, safflower oil, or soybean oil, safflower oil. Among them, liquid paraffin, and a vegetable oil component, such as jojoba oil, are particularly preferred.

Further, a silicone oil, such as a chain silicone (for example, dimethicone, methyl phenyl polysiloxane (diphenylsiloxy phenyl trimethicone), or methyl hydrogen polysiloxane) and a cyclic silicone (for example, cyclopentasiloxane, tetrahydro tetramethylcyclotetrasiloxane, octamethylcyclotetrasiloxane, decamethylcyclopentasiloxane, or dodecamethylcyclohexasiloxane), and a fluorine carbonate oil, such as FOMBLIN series (available from AUSIMONT) can also be used.

Further, a semi-solid oil-based component, such as hardened palm oil, hardened castor oil, or vaseline, and a solid oil component, such as paraffin wax, microcrystalline wax, carnauba wax, or candelilla wax, can also be used.

In particular, in the case of the thickened composition of the disclosure, it is preferred that the oil-based component has a melting point of around 37° C. or lower so that the oil-based component melts on the skin; however, a small amount of solid oil component, such as a wax, can be blended.

The amount of the oil component to be blended may be a balance relative to the total amount of other essential components and optional additives contained in the thickened composition of the disclosure, and is preferably in the range from 35 to 85 mass % in the disclosure. If the amount of the oil-based component is excessively small, the resulting thickened composition is not elastic. On the other hand, if the amount of the oil-based component is excessively large, it is difficult to include bubbles in the resulting thickened composition.

Other Powder Components

The thickened composition of the disclosure may also contain powder components other than the above-described fine particulate powder. Usable powder components are not particularly limited as long as they are commonly used in cosmetics, and examples thereof may include: inorganic powders, such as talc, mica, kaolin, mica, sericite, muscovite, phlogopite, synthetic mica, synthetic mica, lepidolite, biotite, lepidolite, vermiculite, magnesium carbonate, calcium carbonate, aluminum silicate, barium silicate, calcium silicate, magnesium silicate, strontium silicate, metal tungstate salt, magnesium, spherical silica, zeolite, barium sulfate, calcined calcium sulfate, calcium phosphate, fluorapatite, hydroxyapatite, ceramic powder, metal soap (such as zinc myristate, calcium palmitate, aluminum stearate), and boron nitride; spherical organic powders, such as polyamide spherical resin powder (nylon spherical powder), spherical polyethylene, cross-linked poly(methyl (meth)acrylate) spherical resin powder, spherical polyester, cross-linked polystyrene spherical resin powder, stylene/acrylic acid copolymer spherical resin powder, benzoguanamine spherical resin powder, polyethylene tetrafluoride spherical powder, and spherical cellulose; inorganic white pigments, such as zinc oxide, barium sulfate, and zinc oxide coated or combined with anhydrus silicate; inorganic red pigments, such as iron oxide (colcothar), and iron titanate; inorganic brown pigments, such as γ-iron oxide; inorganic yellow pigments, such as yellow iron oxide, and ocher; inorganic black pigments, such as black iron oxide, carbon black, and low-valence titanium oxide; inorganic violet pigments, such as mango violet, and cobalt violet; inorganic green pigments, such as chromium oxide, chromium hydroxide, and cobalt titanate; inorganic blue pigments, such as ultramarine, and iron blue; and pearl and lame materials, such as mica titanium, colcothar-coated mica, colcothar-coated mica titanium, carmine-coated mica titanium, iron blue-coated mica titanium, titanium oxide-coated synthetic phlogopite, colcothar/titanium oxide-coated synthetic phlogopite, titanium oxide-coated glass flakes, colcothar/titanium oxide-coated glass flakes, titanium oxide-coated alumina flakes, titanium oxide-coated silica flakes, iron oxide/silica-coated aluminum, iron oxide/silica-coated iron oxide, metal-coated tabular powder, polyethylene terephthalate/polymethyl methacrylate-laminated film powder (which may contain a colorant), polyethylene terephthalate/polyolefin-laminated film powder (which may contain a colorant), epoxy resin-coated aluminum-deposited polyethylene terephthalate (which may contain a colorant), aluminum-deposited polyethylene terephthalate (which may contain a colorant), urethane resin-coated aluminum-deposited polyethylene terephthalate (which may contain a colorant), acrylic resin-coated aluminum powder (which may contain a colorant), titanium oxide-coated mica, titanium oxide-coated bismuth oxychloride, titanium oxide-coated talc, colored titanium oxide-coated mica, bismuth oxychloride, and argentine.

The other powder components are contained preferably in an amount of not less than 1 mass % and not more than 25 mass %, and more preferably in an amount of not less than 3 mass % and not more than 15 mass % relative to the total mass of the thickened composition.

Further, the total powder components including the fine particulate powder are contained preferably in an amount of not less than 1 mass % and not more than 40 mass %, and more preferably in an amount of not less than 10 mass % and not more than 30 mass % relative to the total mass of the thickened composition. Including the total powder components in an amount of not less than 1 mass % allows suppressing stickiness, and including the total powder components in an amount of not more than 40 mass % allows providing smooth feel.

Among the above-described other powder components, the spherical powder, such as spherical polyethylene, polyamide spherical resin powder (nylon spherical powder), or cross-linked poly(methyl (meth)acrylate) spherical resin powder, the extender pigment, such as silica, talc, mica, kaolin, sericite, calcium carbonate, or magnesium carbonate, the silicone powder, such as (diphenyl dimethicone/vinyl diphenyl dimethicone/silsesquioxane) crosspolymer, and the metal soap, etc., are preferably used in view of usability. Further, the pearl and lame materials are also preferably used.

The other powder components may have any of spherical, tabular, or indefinite shapes. Further, the other powder components may or may not be subjected to fluorine treatment. The fluorine treatment may be conducted using any method as long as it can impart water repellency to the powders, and a known hydrophobizing treatment method can be used.

Water

The thickened composition may contain water. Including water in the thickened composition allows emulsifying the oil phase using the thickened composition of the disclosure and the water phase to provide an emulsion with good emulsion stability. This allows using the thickened composition of the disclosure in particular in a W/O type emulsion cosmetic.

The thickened composition of the disclosure may further contain additives that are commonly usable in cosmetics, such as a surfactant, a lower alcohol (such as ethanol), a dispersant, a moisturizer, a cooling agent, an antiperspirant, an UV absorbent, an UV scattering agent, a thickener, an antioxidant, an antiseptic, a disinfectant, a pH controlling agent, a vitamin, a circulation promoter, a skin-lightening agent, a skin activator, an active ingredient, an extract from an animal, or vegetable, a colorant, a perfume, etc., as desired, within a range where the effects of the disclosure are not impaired. The examples given above are not intended to limit the disclosure.

Method of Producing Thickened Composition

The method used to produce the thickened composition of the disclosure is not particularly limited; however, the thickened composition can preferably be obtained by stirring and mixing the silicone crosspolymer having a structure where dimethicone is cross-linked with an organic group, the fine particulate powder, and the other components, as desired, with a disperser at room temperature.

For example, first, a powder formulation, such as one taught in Japanese Patent No. 3812733, may be prepared by charging the silicone crosspolymer having a structure where dimethicone is cross-linked with an organic group, the fine particulate powder, and the other components, as desired, in a container coated with glass, enamel, or fluorine, and then shaking and mixing them.

Examples of devices usable for preparation with shaking and mixing may include a kneader, a homogenizer (which effects stirring using a high-speed rotating shaft having knives), a shaker, a V-shaped mixer (which effects stirring using a rotating V-shaped container), an airflow stirring mixer, a horizontal cylinder mixer, a double cone mixer, a ribbon mixer, and a high speed flow type mixer. An example of a device that sprays the oil-based components while stirring the powder components is an oil spray-type rocking mixer.

It should be noted that, in a case of small volume production, a compact mixer that creates an open system hydrophobic space, such as a sample mill, a magnetic stirrer, a disperser, a homomixer, POLYTRON, THREE ONE MOTOR, may also preferably be used.

The thickened composition of the disclosure may, for example, be a skin care cosmetic, such as cream, a makeup cosmetic, such as foundation, makeup base, blusher, or eye shadow, or a sunscreen cosmetic; however, these examples are not intended to limit the disclosure.

The thickened composition of the disclosure is a composition that take a whip-like, souffle-like, marshmallow-like, or paste-like form, can be taken well, can be uniformly spread when applied to the skin, and can provide smoothness and silky touch.

EXAMPLES

Hereinafter, the cosmetic product of the disclosure is described in further detail by way of examples, which are not intended to limit the disclosure.

First, a description is given on cosmetics used in examples of the disclosure and comparative examples.

Example 1-1

A thickened composition (foundation) was prepared according to the above-described method of producing the thickened composition using the components shown below.

| | |
|---|---|
| Decamethyl cyclopentane siloxane (*6) | 43 mass % |
| Dimethicone | 16 mass % |
| Dimethicone crosspolymer (*1) | 5 mass % |
| Fine particulate titanium Oxide (*2) | 10 mass % |
| Silica (*3) | 4 mass % |
| (Diphenyl dimethicone/vinyl diphenyl dimethicone/ silsesquioxane) crosspolymer (*4) | 4 mass % |
| Diphenylsiloxy phenyl trimethicone (*5) | 4 mass % |
| Ethylhexyl methoxycinnamate | 3 mass % |
| DPG (dipropylene glycol) | appropriate amount |
| Safflower oil | appropriate amount |
| Sodium hyaluronate | appropriate amount |
| Alumina | appropriate amount |
| Glycerin | appropriate amount |
| Tetrahydro tetramethylcyclotetrasiloxane | appropriate amount |
| Disteardimonium hectorite | appropriate amount |

Details of the compounds used in the above production example 1 are shown below.
(*1) Provided as DOW CORNING 9045 SILICONE ELASTOMER BLEND available from Dow Corning Toray. The amount of the dimethicone crosspolymer was calculated from the actual content.
(*2) TITANIUM DIOXIDE (TTO-V-4) (having an average primary particle diameter of 0.01 μm) available from Ishihara Sangyo Kaisha, Ltd.
(*3) SUNSPHERE L-51S (having an average particle diameter of 5 μm) available from Dohkai Chemical Industries Co., Ltd.
(*4) KSP-300 available from Shin-Etsu Chemical Co., Ltd.
(*5) KF-56 available from Shin-Etsu Chemical Co., Ltd.
(*6) The total amount of the portion provided as DOW CORNING 9045 and a portion added as a solvent.

The storage modulus G', the loss modulus G", and the loss tangent tan δ of the resulting foundation are shown in Table 1. The resulting foundation was elastic and fluffy.

Example 1-2

A foundation was prepared in the same manner as in Example 1-1 except that the amount of the dimethicone crosspolymer was 4 mass %. The storage modulus G', the loss modulus G", and the loss tangent tan δ of the resulting foundation are shown in Table 1. The resulting foundation was elastic and fluffy.

Example 1-3

A foundation was prepared in the same manner as in Example 1-1 except that the amount of the dimethicone crosspolymer was 4.5 mass %. The storage modulus G', the loss modulus G", and the loss tangent tan δ of the resulting foundation are shown in Table 1. The resulting foundation was elastic and fluffy.

Example 1-4

A foundation was prepared in the same manner as in Example 1-1 except that the amount of the other powders was adjusted to obtain the vales of the storage modulus G', the loss modulus G", and the loss tangent tan δ shown in Table 1. The resulting foundation was elastic and fluffy.

Example 1-5

A foundation was prepared in the same manner as in Example 1-1 except that the amount of the fine particulate titanium oxide was 8 mass %. The storage modulus G', the loss modulus G", and the loss tangent tan δ of the resulting foundation are shown in Table 1. The resulting foundation was elastic and fluffy.

Comparative Example 1-1

A foundation was prepared in the same manner as in Example 1-1 except that the amount of the fine particulate titanium oxide was 6 mass %. The storage modulus G', the loss modulus G", and the loss tangent tan δ of the resulting foundation are shown in Table 2. The resulting foundation exhibited slightly weaker elasticity when compared to Examples 1-1 to 1-5.

Comparative Example 1-2

A foundation was prepared in the same manner as in Example 1-1 except that the amount of the fine particulate titanium oxide was 4 mass %. The storage modulus G', the loss modulus G", and the loss tangent tan δ of the resulting foundation are shown in Table 2. The resulting foundation exhibited slightly weaker elasticity when compared to Examples 1-1 to 1-5.

Comparative Example 1-3

A water-in-oil (W/O) foundation was prepared using the raw materials shown below. The storage modulus G', the loss modulus G", and the loss tangent tan δ of the resulting foundation are shown in Table 2. The resulting foundation exhibited slightly weaker elasticity when compared to Examples 1-1 to 1-5.

| | |
|---|---|
| Water | appropriate amount |
| Butylene glycol | 8 mass % |
| Isohexadecane | 8 mass % |
| Titanium oxide* | 8 mass % |
| Diisopropyl sebacate | 5 mass % |
| Octocrylene | 5 mass % |
| Dimethicone | 4 mass % |
| Alcohol | 4 mass % |

-continued

| | |
|---|---|
| Glycerin | 4 mass % |
| Triethylhexanoin | 4 mass % |
| Cetyl ethylhexanoate | 4 mass % |
| Isopropyl myristate | 3 mass % |
| Polymethylsilsesquioxane | 3 mass % |
| (Dimethicone/vinyl dimethicone) crosspolymer | 3 mass % |
| Polymethyl methacrylate | 3 mass % |
| Lauryl PEG-9 polydimethylsiloxyethyl dimethicone | 3 mass % |
| T-butyl methoxy dibenzoyl methane | 3 mass % |
| Disteardimonium hectorite | 3 mass % |
| PEG/PPG-14/7 dimethyl ether | 2 mass % |
| Hydrogenated polydecene | 2 mass % |
| Cetyl PEG/PPG-10/1 dimethicone | 1 mass % |
| Sorbitan sesquiisostearate | 1 mass % |
| Trehalose | 1 mass % |
| Bis ethylhexyloxyphenol methoxyphenyl triazine | 1 mass % |
| Diethylamino hydroxybenzoyl hexyl benzoate | 1 mass % |
| Iron oxide* | 3 mass % |

(*The other powder components)

Comparative Example 1-4

A liquid crystal oil-in-water (O/W) foundation was prepared using the raw materials shown below. The storage modulus G', the loss modulus G", and the loss tangent tan δ of the resulting foundation are shown in Table 2. The resulting foundation was sticky.

| | |
|---|---|
| Water | appropriate amount |
| Pentaerythritol tetra-2-ethylhexanoate | 15 mass % |
| Glycerin | 10 mass % |
| Butylene glycol | 8 mass % |
| Decamethylcyclopentasiloxane | 5 mass % |
| Behenyl alcohol | 3 mass % |
| Myristyl myristate | 2 mass % |
| Sorbitan tristearate | 1 mass % |
| Erythritol | 1 mass % |
| Xylitol | 1 mass % |
| Glyceryl triisostearate | 1 mass % |
| Stearyl alcohol | 1 mass % |
| Polyethylene glycol monostearate | 1 mass % |
| Self-emulsifying glycol monostearate | 0.5 mass % |
| Polyoxyethylene behenyl ether | 0.5 mass % |
| Polyacrylate salt | 0.2 mass % |
| Sodium citrate | 0.1 mass % |
| Trisodium edetate | 0.1 mass % |
| Citric acid | 0.1 mass % |

Comparative Example 1-5

An α gel oil-in-water (O/W) foundation was prepared using the raw materials shown below. The storage modulus G', the loss modulus G", and the loss tangent tan δ of the resulting foundation are shown in Table 2. The resulting foundation was sticky.

| | |
|---|---|
| Water | appropriate amount |
| Pentaerythritol tetra-2-ethylhexanoate | 13 mass % |
| Glycerin | 10 mass % |
| Butylene glycol | 8 mass % |
| Squalane | 4 mass % |
| Glyceryl triisostearate | 4 mass % |
| Behenyl alcohol | 3 mass % |
| Maltitol | 2 mass % |
| Vaseline | 2 mass % |
| Isodecyl pivalate | 2 mass % |
| Talc | 2 mass % |
| Methylpolysiloxane | 1 mass % |
| Trehalose | 1 mass % |
| Heavy liquid isoparaffin | 1 mass % |
| Stearyl alcohol | 1 mass % |
| Polyoxyethylene behenyl ether | 1 mass % |
| Myristyl myristate | 0.5 mass % |
| Anhydrus silicate | 0.5 mass % |
| Microcrystalline wax | 0.5 mass % |
| Trisodium edetate | 0.1 mass % |
| Sodium citrate | 0.1 mass % |
| Citric acid | 0.1 mass % |

The storage modulus G', the loss modulus G", and the loss tangent tan δ of the above-described cosmetics of Examples 1-1 to 1-5, and Comparative Examples 1-1 to 1-5 were measured as described below.

Storage Modulus G'

The storage modulus G' was measured using a rheometer MCR301 available from Anton Paar, under the conditions of a gap of 0.5 mm, a strain oscillation angle of 0.1%, a frequency of 1 Hz, and a temperature of 25° C. while increasing stress applied with a 25 mm φ cone plate.

Loss Modulus G"

The loss modulus G" was measured using the rheometer MCR301 available from Anton Paar, under the conditions of a gap of 0.5 mm, a strain oscillation angle of 0.1%, a frequency of 1 Hz, and a temperature of 25° C. while increasing stress applied with a 25 mm φ cone plate.

Loss Tangent Tan δ

The loss tangent tan δ was calculated by G"/G' based on the values of G' and G" that were measured using the rheometer MCR301 available from Anton Paar as described above.

The results of the measurements are shown in Tables 1 and 2.

TABLE 1

| | | Example 1-1 | Example 1-2 | Example 1-3 | Example 1-4 | Example 1-5 |
|---|---|---|---|---|---|---|
| Cosmetic | | thickened composition | thickened composition | thickened composition | thickened composition | thickened composition |
| Components | Dimethicone partial crosspolymer | 5 | 4 | 4.5 | 5 | 5 |
| | Fine particulate titanium oxide | 10 | 10 | 10 | 10 | 8 |
| Physical properties | Storage modulus G' (Pa) | 6190 | 3750 | 4290 | 6010 | 3810 |
| | Loss modulus G" (Pa) | 768 | 674 | 679 | 697 | 514 |
| | Loss tangent tan δ | 0.124 | 0.180 | 0.158 | 0.116 | 0.135 |
| | (Strain oscillation angle 0.1%) | elastic (fluffy) | elastic (fluffy) | elastic (fluffy) | elastic (fluffy) | elastic (fluffy) |

TABLE 2

|  |  | Comp. Ex. 1-1 | Comp. Ex. 1-2 | Comp. Ex. 1-3 | Comp. Ex. 1-4 | Comp. Ex. 1-5 |
|---|---|---|---|---|---|---|
| Cosmetic |  | thickened composition | thickened composition | W/O | liquid crystal O/W | α gel O/W |
| Components | Dimethicone partial crosspolymer | 5 | 5 | 3 | — | — |
|  | Fine particulate titanium oxide | 6 | 4 | — | — | — |
| Physical properties | Storage modulus G' (Pa) | 2990 | 2620 | 2520 | 5600 | 616 |
|  | Loss modulus G" (Pa) | 322 | 313 | 124 | 1400 | 185 |
|  | Loss tangent tan δ (Strain oscillation angle 0.1%) | 0.108 weaker elasticity | 0.119 weaker elasticity | 0.049 weaker elasticity | 0.250 sticky | 0.300 sticky |

Next, examples of the cosmetic of the disclosure and comparative examples are shown.

Examples 2-1 to 2-2, Comparative Examples 2-1 to 2-7

Example 2-1

A cosmetic product was prepared using the cosmetic (foundation) of Example 1-1 and the container provided with the mesh material shown in FIG. 1 (which will hereinafter be referred to as container). First, the foundation of Example 1-1 was put in the container body, and then the inner lid was fit into the container body. Then, the foundation was taken with a hand through the mesh material by pressing the mesh material, and applied to the skin.
The inner diameter of the container body: 60 mm φ
The inner diameter of the inner lid: 57 mm φ
The mesh material: nylon/polyurethane (having a mesh opening size of 0.5 mm, and a wire diameter of around 0.3 mm)

Example 2-2

The foundation of the cosmetic product of Example 2-1 was taken using a puff (polyurethane) and applied to the skin.

Comparative Example 2-1

The foundation of Example 1-1 was put in a tube-type container (having an opening diameter of 2 mm φ), and then taken with a hand by pressing the middle portion of the tube, and applied to the skin.

Comparative Example 2-2

The foundation of Example 1-1 was put in a tube-type container (having an opening diameter of 2 mm φ), and then taken with a puff (polyurethane) by pressing the middle portion of the tube, and applied to the skin.

Comparative Example 2-3

The foundation of Example 1-1 was put in a jar. Then, the foundation was taken with a hand, and applied to the skin. It should be noted that the jar used here was the container without the inner lid provided with a tight mesh material.

Comparative Example 2-4

The foundation of Example 1-1 was put in a jar. Then, the foundation was taken with a puff (polyurethane), and applied to the skin.

Comparative Example 2-5

The foundation of Comparative Example 1-3 (an oil-in-water (W/O) foundation) was put in the container body of the container with the mesh inner lid. Then, the foundation was taken through the mesh material with a puff (polyurethane) by pressing the mesh material with the puff, and applied to the skin.

Comparative Example 2-6

The foundation of Comparative Example 1-4 (a liquid crystal water-in-oil (O/W) foundation) was put in the container body of the container with the mesh inner lid. Then, the foundation was taken through the mesh material with a puff (polyurethane) by pressing the mesh material with the puff, and applied to the skin.

Comparative Example 2-7

The foundation of Comparative Example 1-5 (α gel oil-in-water (O/W) foundation) was put in the container body of the container with the mesh inner lid. Then, the foundation was taken through the mesh material with a puff (polyurethane) by pressing the mesh material with the puff, and applied to the skin.
Evaluation Ten professional panelists used each sample of the above-described cosmetic products of the examples and the comparative examples, and then scored each sample according to questionnaire with respect to spreadability, silky touch, smoothness, ease of taking the thickened composition, and uniformity when the thickened composition was applied.
Scores
1: Very dissatisfied
2: Dissatisfied
3: Slightly dissatisfied
4: Neutral
5: Slightly satisfied
6: Satisfied
7: Very satisfied
Evaluation Evaluation was conducted by calculating average scores of ten panelists and according to the criteria shown below.
AA: 6 points or more
A: 5 points or more and less than 6 points
B: 3 points or more and less than 5 points
C: less than 3 points
The results of the evaluation are shown in Table 3.

TABLE 3

|  |  | Example 2-1 | Example 2-2 | Comp. Ex. 2-1 | Comp. Ex. 2-2 | Comp Ex. 2-3 | Comp. Ex. 2-4 | Comp. Ex. 2-5 | Comp. Ex. 2-6 | Comp. Ex. 2-7 |
|---|---|---|---|---|---|---|---|---|---|---|
| Cosmetic product | Cosmetic (foundation) | Example 1-1 | Example 1-1 | Example 1-1 | Example 1-1 | Example 1-1 | Example 1-1 | Comp. Ex. 1-3 | Comp. Ex. 1-4 | Comp. Ex. 1-5 |
|  | Container | container with mesh material | container with mesh material | tube | tube | jar | jar | container with mesh material | container with mesh material | container with mesh material |
| Tool |  | hand | puff | hand | puff | hand | puff | puff | puff | puff |
| Evaluation | Spreadability | A | A | A | A | A | A | C | C | C |
|  | Silky touch | A | A | A | A | A | A | C | C | C |
|  | Smoothness | A | A | A | A | A | A | C | C | C |
|  | Ease of taking thickened composition | A | AA | D | D | D | D | A | A | A |
|  | Uniformity when applied | A | AA | D | C | D | C | C | C | C |

As shown in Table 3, the cosmetic products of the disclosure were evaluated as A or higher for all the evaluation items. In particular, the ease of taking the thickened composition and the uniformity when applied were better when the composition was taken with a puff than when the composition was taken with a hand.

On the other hand, Comparative Examples 2-1 and 2-2, which used the tube container, and Comparative Examples 2-3 and 2-4, which used the jar container without the mesh material, were evaluated poorer with respect to the ease of taking the thickened composition and the uniformity when applied.

Further, Comparative Example 2-5, which used the oil-in-water (W/O) foundation as the composition, Comparative Example 2-6, which used the liquid crystal water-in-oil (O/W) foundation as the composition, and Comparative Example 2-7, which used the α gel O/W foundation as the composition, were evaluated poorer with respect to the spreadability, the silky touch, the smoothness, and the uniformity when applied.

EXPLANATION OF THE REFERENCE NUMERALS

10: cosmetic product
11: container
12: container body
13: inner lid
14: outer lid
21: frame
22: lower end
23: mesh material
24: bottom surface
25: edge

The invention claimed is:

1. A thickened composition for a cosmetic product including a content that is taken through a mesh material, the thickened composition comprising:
   a silicone crosspolymer having a structure where dimethicone is cross-linked with an organic group in an amount of not more than 10 mass % relative to the total mass of the thickened composition, the silicone crosspolymer including at least a dimethicone crosspolymer and a (diphenyl dimethicone/vinyl diphenyl dimethicone/silsesquioxane) crosspolymer;
   titanium dioxide as a fine particulate powder having an average primary particle diameter of not more than 0.01 μm in an amount of not less than 8 mass % and not more than 15 mass % relative to the total mass of the thickened composition; and
   an oil component including at least one selected from a group consisting of decamethyl cyclopentane siloxane, dimethicone, diphenylsiloxy phenyl trimethicone and ethylhexyl methoxycinnamate in an amount of not more than 85 mass % relative to the total mass of the thickened composition,
   wherein a storage modulus G' of the thickened composition is not less than 3750 Pa, which is measured with a rheometer under the conditions of a gap of 0.5 mm, a strain oscillation angle of 0.1%, a frequency of 1 Hz, and a temperature of 25° C. while increasing stress applied with a 25 mm φ cone plate, and a loss tangent tan δ of the thickened composition is not more than 0.2, which is calculated as a loss modulus G" measured under the same conditions divided by the storage modulus G'.

2. The thickened composition as claimed in claim 1, wherein the silicone crosspolymer having a structure where dimethicone is cross-linked with an organic group is contained in an amount of not less than 2 mass % and not more than 10 mass % relative to the total mass of the thickened composition.

3. The thickened composition as claimed in claim 1, wherein the silicone crosspolymer having a structure where dimethicone is cross-linked with an organic group comprises a dimethicone crosspolymer.

4. The thickened composition as claimed in claim 1, wherein the mesh material has a mesh opening size of not less than 0.1 mm.

5. The thickened composition as claimed in claim 1, wherein the thickened composition comprises water.

6. A cosmetic product comprising:
   a container comprising a container body having an upper opening, an inner lid provided with a tight mesh material, and an outer lid configured to tightly close the container body; and
   the thickened composition as claimed in claim 1 contained in the container body under the inner lid such that the thickened composition is able to be taken through the mesh material.

7. The cosmetic product as claimed in claim 6, wherein the thickened composition is taken using a puff.

8. The thickened composition as claimed in claim 2, wherein the silicone crosspolymer having a structure where dimethicone is cross-linked with an organic group comprises a dimethicone crosspolymer.

9. The thickened composition as claimed in claim 2, wherein the mesh material has a mesh opening size of not less than 0.1 mm.

10. The thickened composition as claimed in claim 3, wherein the mesh material has a mesh opening size of not less than 0.1 mm.

11. The thickened composition as claimed in claim 2, wherein the thickened composition comprises water.

12. A cosmetic product comprising:
  a container comprising a container body having an upper opening, an inner lid provided with a tight mesh material, and an outer lid configured to tightly close the container body; and
  the thickened composition as claimed in claim 2 contained in the container body under the inner lid such that the thickened composition is able to be taken through the mesh material.

13. The cosmetic product as claimed in claim 12, wherein the thickened composition is taken using a puff.

14. The thickened composition as claimed in claim 1, wherein the oil component is contained in an amount of not less than 35 mass % and not more than 85 mass % relative to the total mass of the thickened composition.

* * * * *